United States Patent
Krayss et al.

(10) Patent No.: US 10,215,729 B2
(45) Date of Patent: Feb. 26, 2019

(54) METHOD OF MONITORING THE DRY CLEANING PROGRESS OF A TRANSCUTANEOUS SENSOR

(71) Applicant: Radiometer Basel AG, Basel (CH)

(72) Inventors: Florian Krayss, Riehen (CH);
Hansruedi Vogt, Erschwil (CH);
Dominik Liechty, Münchenstein (CH);
Christian Bochud, Bienne (CH)

(73) Assignee: Radiometer Basel AG, Basel (CH)

(*) Notice: Subject to any disclaimer, the term of this patent is extended or adjusted under 35 U.S.C. 154(b) by 72 days.

(21) Appl. No.: 15/257,553

(22) Filed: Sep. 6, 2016

(65) Prior Publication Data

US 2017/0067851 A1    Mar. 9, 2017

(30) Foreign Application Priority Data

Sep. 7, 2015  (DK) .................................. 2015 00530

(51) Int. Cl.
| | | |
|---|---|---|
| *G01N 27/416* | (2006.01) | |
| *A61B 5/145* | (2006.01) | |
| *A61B 5/1477* | (2006.01) | |
| *A61B 5/1473* | (2006.01) | |
| *B08B 1/00* | (2006.01) | |

(52) U.S. Cl.
CPC ....... *G01N 27/4163* (2013.01); *A61B 5/1473* (2013.01); *A61B 5/1477* (2013.01); *A61B 5/14542* (2013.01); *B08B 1/006* (2013.01); *A61B 2562/245* (2013.01)

(58) Field of Classification Search
None
See application file for complete search history.

(56) References Cited

U.S. PATENT DOCUMENTS

| | | | |
|---|---|---|---|
| 3,661,748 A | 5/1972 | Blackmer | |
| 4,789,453 A | 12/1988 | Eberhard et al. | |
| 5,007,424 A | 4/1991 | Ahsbahs et al. | |
| 7,232,511 B1 | 6/2007 | Venkatasetty | |
| 9,182,280 B1* | 11/2015 | Gardner | ................ G01J 3/0297 |
| 2007/0267039 A1* | 11/2007 | Sullivan | .................... B08B 3/12 |
| | | | 134/1 |

(Continued)

FOREIGN PATENT DOCUMENTS

EP      0 346 083 A2    12/1989

OTHER PUBLICATIONS

Tyszczuk, Katarzyna et al., "Voltammetric method using a lead film electrode for the determination of caffeic acid in a plant material," Food Chemistry, vol. 125, pp. 1498-1503 (2011).

(Continued)

*Primary Examiner* — Nicole Blan
(74) *Attorney, Agent, or Firm* — Finnegan, Henderson, Farabow, Garrett & Dunner, LLP

(57) ABSTRACT

The proposed invention provides a method of monitoring the dry cleaning progress of a transcutaneous sensor having an electrode for measuring $pCO_2$ and an electrode for measuring $pO_2$, both electrodes opening into a measuring surface of the sensor. The method comprises receiving an AC signal from the $pCO_2$ electrode, initiating a cleaning of the sensor, and monitoring the cleaning progress by analyzing AC signals subsequently received from the $pCO_2$ electrode.

17 Claims, 2 Drawing Sheets

(56) References Cited

U.S. PATENT DOCUMENTS

2014/0148665 A1\* 5/2014 Bernstein ............ A61B 5/14532
600/345
2015/0212042 A1 7/2015 Newton et al.
2015/0359599 A1\* 12/2015 Fagan .................... A61B 1/121
134/18

OTHER PUBLICATIONS

European Search Report for European Patent Application No. EP 16 18 7028, dated Jan. 19, 2017.
Danish Patent and Trademark Office Search Report for Application No. PA 2015 00530, dated Apr. 12, 2016 (4 pages).

\* cited by examiner

METHOD OF MONITORING THE DRY CLEANING PROGRESS OF A TRANSCUTANEOUS SENSOR

FIELD OF THE INVENTION

This application claims the benefit of priority to Denmark Patent Application No. PA 2015 00530, filed Sep. 7, 2015, the entire contents of which are herein incorporated by reference in their entirety.

The invention relates to a method of monitoring the dry cleaning progress of a transcutaneous sensor having a sensor for measuring $pCO_2$ and a sensor electrode for measuring $pO_2$, both electrodes opening into a measuring surface of the sensor. The invention further relates to a monitor for monitoring the cleaning progress.

BACKGROUND

The transcutaneous (TC) non-invasive measurement of the partial pressure of blood gases such as carbon dioxide ($pCO_2$) or oxygen ($pO_2$) by means of a TC electrochemical sensor applied to the skin has been described in many publications as a useful tool in a number of clinical situations. An electrochemical sensor for such use is known from e.g. U.S. Pat. No. 6,654,622 B1. Incorporated in and opening into the measuring surface of such electrochemical sensor are both an electrode for measuring $pCO_2$ and an electrode for measuring $pO_2$ as well as a reference electrode.

TC electrochemical sensors comprise among others a membrane system covering the surface of the sensor and an electrolyte solution placed between the membrane and the measuring surface. The electrolyte solution creates a bridge for electrons between the $pCO_2$ electrode and the $pO_2$ electrode of the sensor.

In the most common TC electrochemical sensors, the $pCO_2$ electrode comprises a pH glass electrode and the $pO_2$ electrode comprises a cathode. e.g. a Pt cathode. However, it has long been known that during use of the TC sensor a growth of metallic material (dendrites) builds up on the measuring surface and around the measuring surface of the cathode. The dendrite material origins from metals parts of the sensor in the sensor, thus usually silver, but also gold in minor amounts have seen to appear. The growing of dendrites means that the surface of the cathode increases over time. This increase is found to be not linear but of a higher degree order. The increase of the cathode sensor area increases the sensitivity of the $pO_2$ electrode. Once a predefined sensitivity limit is reached, the sensor is not capable to be calibrated and has to be refurbished. Furthermore, an increased sensitivity results in a linearity deviation, which limits the sensor accuracy on the extreme measurement ranges.

To overcome the problems of dendrites on the Pt cathode surface, the sensor measuring surface has to be cleaned from time to time. The user may be instructed to clean the sensor from time to time, depending on the usage of the sensor or alternatively an upper sensitivity threshold may be defined, such that when this sensitivity threshold is reached, the user is instructed to clean the sensor independently of when the sensor was cleaned the last time. Manuals have instructed the user to thoroughly clean the sensor, but as the dendrites on a Pt cathode are too small to be seen by the human eye, it has been difficult for the user to understand what thorough cleaning meant. If the sensor is not cleaned properly this may result in failure of calibration of the sensor. As the dendrites stick to the Pt cathode and cannot just be "washed away" with a wet cloth (since silver and gold are not soluble in any cleaning agents), it is necessary to scrub or grind the dendrites of the cathode in a so-called dry cleaning process wherein the dry measuring surface is scrubbed with a dry cloth.

If the sensor is not cleaned sufficiently by the user, so as to remove the dendrites, the time before next cleaning decreases and as the growth increases to a higher degree, the time between cleaning consequently fails increasingly fast. This is of course inconvenient and time consuming for the user and as every cleaning of the sensor requires replacement of the membrane system and electrolyte solution it also requires use of extra membrane systems/electrolyte solution. Furthermore, it leads to shorter life time of the sensor, and if not dealt with, makes the measurements unreliable.

One way to overcome the frequent cleaning and reduced sensor life time could be to accept the higher sensitivity which would decrease the reliability of the measured partial pressure of oxygen, due to an increased linearity deviation of the sensor. This would limit the measurement in the extreme measurement range as e.g. (1) patients in hyperbaric chamber or (2) preterm neonates with very low $pO_2$ values due to insufficient oxygen titration, or (3) patients with reduced blood perfusion.

Another solution provided in the field has been to provide a special tool for the dry cleaning step wherein the sensor is placed inside a tool, where it sits firmly and the tool is closed firm around the sensor. The user than turns a knob on the tool whereby rotating disks clean the sensor. This has the advantage that it is a standard cleaning process. It provides a cleaning method better than a very poor and slobby manual cleaning using a cloth, but with the disadvantage of an extra tool necessary for the user and with the risk of "overcleaning" (destroying the sensor surface).

The object of the invention is to provide a method for monitoring the cleaning progress when the user cleans the sensor and further to provide feedback to the user about the cleaning progress of the sensor. The method provides the user of TC electrochemical sensors with means for determining how well the cathode has been cleaned, or how much more cleaning is necessary before the cathode is clean.

SUMMARY OF THE INVENTION

In a first aspect of the present invention, the applicant makes available a method of monitoring the dry cleaning progress of a transcutaneous sensor having an electrode for measuring $pCO_2$ and an electrode for measuring $pO_2$, both electrodes opening into a measuring surface of the sensor. The method comprises receiving an AC signal from the $pCO_2$ electrode, initiating a cleaning of the sensor, and monitoring the cleaning progress by analyzing AC signals subsequently received from the $pCO_2$ electrode.

The inventors found that the mechanical scrubbing of the measuring sensor surface with a dry cloth creates small AC signals at the $pCO_2$ electrode. Further, they found that these created AC signals do not look like the physiological signal that this sensor usually picks up when measuring $pCO_2$. Thus, by analyzing the signals it is possible to monitor the cleaning progress of the sensor and thereby verify that a sensor is being cleaned and to what extent the sensor has been cleaned.

In some example embodiments, initiating the cleaning of the sensor comprises a user manually starting the cleaning.

A user may manually start the cleaning by providing input to the system that controls the sensor. This could e.g. be done by the user pressing a specific cleaning button on an input screen of a monitor connected to the sensor.

In some example embodiments, initiating the cleaning of the sensor comprises determining that the AC signal is a cleaning signal.

Electrodes for detecting $pCO_2$ uses the voltage across the electrodes of the sensor to determine the carbon dioxide. Thus, both the sensor and a processor connected to or incorporated into the sensor are already suited for receiving and detecting AC signals. As the AC signals created at the $pCO_2$ electrode during dry cleaning differ from the signals normally received, it may be possible for the processor to recognize a signal as a cleaning signal and initiate a cleaning. In this case, the processor only has to be programmed to recognise these cleaning signals.

The strength of the cleaning signal depends on how firmly the user scrubs on the surface of the sensor with the cloth and on the material of the cloth. Usually the dry cleaning will create $pCO_2$ electrode AC signals in the 1-to-10 mV range.

In some example embodiments the AC signals received from initiating the cleaning provides a signal function f(t).

Providing a signal function f(t) of the AC signals received makes it convenient to use analysis of the function f(t) in monitoring the cleaning progress. Further, this allows the cleaning progress to be evaluated over time looking at the recent history.

In some example embodiments the cleaning progress is determined by analysis of derivatives of the signal function f(t), e.g. analysis of first and/or second derivatives of the signal function f(t).

Using the derivatives of the signal function f(t) opens up the possibility of providing a very thorough analysis of the AC signals received by the $pCO_2$ electrode in response to the cleaning by the user.

In some example embodiments the cleaning progress is determined in cleaning intervals, each interval being generated when a predetermined criteria has been met. Further, the sensor may be determined to be clean when a predetermined number of intervals have been performed.

Thus, the system makes it possible to monitor the cleaning progress in steps and determine when the sensor has been sufficiently cleaned.

In some example embodiments the method includes informing the user of the status of the cleaning progress.

By informing the user of the progress, the user knows how much more cleaning is necessary, but also learns how the sensor is best cleaned and gets an understanding of how the pressure and intensity applied during cleaning affects the progress. Hence the user will also learn to clean the sensor more efficiently.

In some example embodiments the information to the user is provided by a monitor connected to the sensor. The monitor may communicate with the sensor using cables or wireless transmission means.

The method may also be implemented in a signal processor located in a TC sensor, and the result of the cleaning process analysis may be sent to a monitor or a screen on an external device using wired or wireless transmission means. The signal processing of analyzing AC signals to determine the cleaning progress may be handled in a processor in the sensor on in the monitor. Independently of whether the analysis is done on the sensor or in the monitor, the signal from the sensor to the monitor may be analogue or digital.

The advantage of transmitting digital signals from the sensor to the screen or monitor is that digital signals are less vulnerable to noise, compared with analogue signals. On the other hand, digital transmission requires at least a D/A converter in the sensor.

In case a monitor is connected to the sensor, the monitor will typically be kept in a cleaning mode as long as the sensor shall be cleaned, thus securing that the user cleans the sensor sufficiently and not starts using it for measurements too early.

According to another aspect of the present invention, the applicant makes available a monitor for monitoring signals measured by a transcutaneous sensor having an electrode for measuring $pCO_2$ and an electrode for measuring $pO_2$, both electrodes opening into a measuring surface of the sensor. The monitor is adapted to monitor the cleaning progress of said transcutaneous sensor by receiving an AC signal from the $pCO_2$ electrode, receiving an input initiating a cleaning of the sensor, monitoring the cleaning progress by analyzing AC signals subsequently received from the $pCO_2$ electrode, and informing the user of the status of the cleaning progress.

A monitor according to this aspect of the invention may provide the user with insight about the cleaning progress, when the user is cleaning the sensor.

According to an embodiment of the second aspect, the monitor is adapted for receiving input from a user and initiating the cleaning of the sensor comprises a user manually starting the cleaning by providing input to the monitor.

According to a further embodiment of the second aspect, the user is informed of the cleaning progress based on a number of cleaning intervals, each interval being generated when a predetermined criteria has been met.

Showing the number of intervals, gives the user a clear indication of how much more cleaning s necessary.

The skilled person will appreciate that the different embodiments may be combined to monitor the cleaning progress and the cleanness of the sensor to a higher degree, than using each embodiment alone.

The invention will now be further described with reference to the figures.

DETAILED DESCRIPTION

Figure 1:
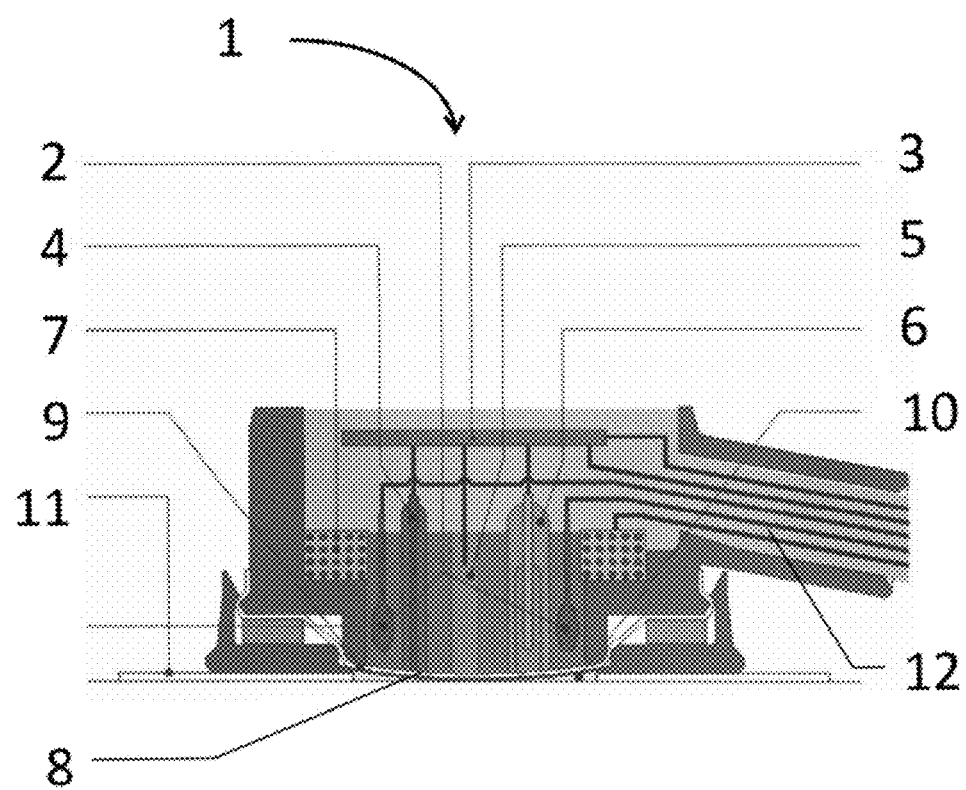
FIG. 1 shows a TC sensor 1 for the method as described herein.

FIG. 1 shows a TC sensor 1 as known in the art. The TC sensor 1 has a temperature sensor 2 in the shape of a thermistor and a buffer amplifier 3 for $pCO_2$ electrode voltage amplification and $pO_2$ electrode current to voltage conversion. The TC sensor 1 further comprises a $pO_2$ measuring electrode 4 in the shape of a Pt cathode, an Ag/AgCl reference electrode 5, a $pCO_2$ electrode 6 comprising a pH glass electrode and a heating element 7 for heating the TC sensor 1 to make the skin permeable for $CO_2$ and especially for $O_2$ The $pO_2$ electrode 4, the reference electrode 5 and the $pCO_2$ electrode 6 all open into a measuring surface 8 of the TC sensor 1. A membrane system 9 covers the measuring surface 8, an electrolyte solution (not shown) being embedded between the membrane system 9 and the measuring surface 8 to secure transfer of the $O_2$ and $CO_2$ diffused through the membrane system 9 to the measuring surface 8. The TC sensor 1 is to be mounted on a patients' skin by means of an adhesive 11 ring, a contact fluid 10 being placed between the skin and the measuring surface 8. The TC sensor 1 is via a cable 12 connected to a monitor (not shown) controlling the functioning of and processing data from the sensor. The TC sensor 1 has an outer diameter of around 15 mm.

When in use dendrites will over time grow on the Pt cathode 4 at the place where it opens into the measuring surface 8, thus increasing the surface of the Pt cathode 4. As mentioned above, this will result in an increase in the sensitivity of the $pO_2$ sensor 4. In order to remove the dendrites the user will have to remove the dendrites from the Pt cathode 4 by cleaning (scrubbing) the measuring surface 8. When cleaning the Pt cathode 4, the user will scrub the entire measuring surface 8 including the surface of the pH glass electrode 6, thus creating a detectable AC signal at the pH glass electrode 6.

Figure 2:
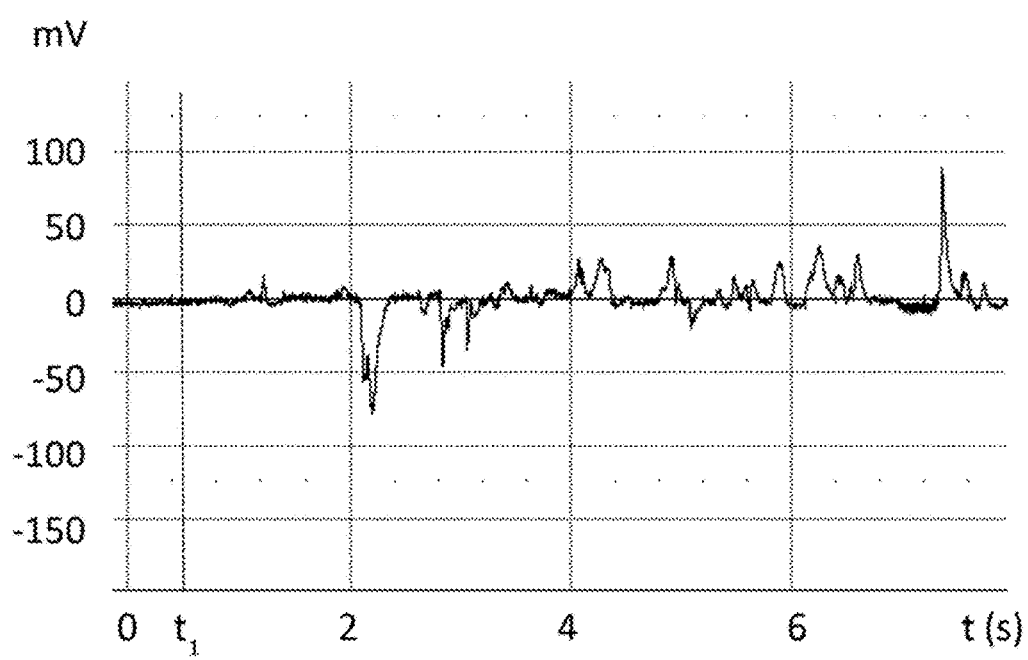
FIG. 2 shows the AC signal measured by the $pCO_2$ electrode as a function of time when cleaning the sensor surface of the TC sensor 1 of FIG. 1.

FIG. 2 shows an example of the recording of the AC signal of the amplified $pCO_2$ signal recorded with a scope as a function f(t) of time during dry cleaning the sensor surface of the TC sensor 1 of FIG. 1.

Prior to the time $t_1$, the TC sensor 1 is in a state where it is held in open air. At $t_1$ a user starts a cleaning process. At first the user presses a "cleaning" button on the monitor screen initiating a cleaning in the system and setting the monitor in cleaning mode. The user then starts scrubbing the measuring surface 8 of the TC sensor 1 with a dry cloth. As can be seen from FIG. 2, the dry cleaning (scrubbing) of the measuring surface results in AC signals received at the $pCO_2$ electrode that are significantly different than the signals received at the $pCO_2$ electrode at the first state (prior to $t_1$). The AC signals are collected from $t_1$ and onwards and processed in the monitor. In this particular system, monitoring of the dry cleaning progress of the TC sensor 1 comprises an analysis of the signal function f(t) using first and second derivatives of the signal function f(t).

Thus, during the monitoring of the signals from the $pCO_2$ electrode, the following averaged values are calculated at 1 Hz:

$$g(t)=abs[d/dt\, f(t)] \quad (1)$$

$$G(t)=d/dt\, abs[f(t)] \quad (2)$$

$$h(t)=abs[d/dt\, g(t)] \quad (3)$$

$$H(t)=d/dt\, abs[g(t)] \quad (4)$$

wherein g(t) is the first derivative, G(t) is the first absolute derivative, h(t) is the $2^{nd}$ derivative, and H(t) is the $2^{nd}$ absolute derivative.

If one of the following criteria (5) and (6) is met, an Interval is generated as a cleaning interval:

$$h(t)>0.26\text{ mV AND }\{g(t)>2.61\text{ mV OR }G(t)>2.61 \text{ mV OR }H(t)>0.65\text{ mV}\} \quad (5)$$

$$h(t)>0.13\text{ mV AND }\{g(t)>2.61\text{ mV AND }G(t)>2.61 \text{ mV AND }H(t)>0.65\text{ mV}\} \quad (6)$$

Each cleaning interval corresponds to the cleaning progress of 10% and thus, the cleaning will be complete after 10 intervals. The cleaning progress is at all times during the cleaning shown at the monitor screen by displaying a window where the user is informed of how far (how many % complete) the cleaning is. During the cleaning, the monitor will remain in cleaning mode.

When the system has reached the 100% cleaning (10 intervals), the dendrites have been removed from the cathode 4. The monitor will then leave cleaning mode and the TC sensor 1 is now ready to receive a new membrane system 9 prior to being used for further measurements of $pCO_2$ and $pO_2$.

The invention claimed is:

1. A method of monitoring a dry cleaning progress of a transcutaneous sensor comprising an electrode for measuring $pCO_2$ and an electrode for measuring $pO_2$, both electrodes opening into a measuring surface of the sensor, the method comprising:
   initiating a cleaning of the sensor,
   receiving an signal from the $pCO_2$ electrode in response to the initiating the cleaning of the sensor,
   monitoring the dry cleaning progress by analyzing AC signals subsequently received from the $pCO_2$ electrode, and
   informing a user of a status of the dry cleaning progress.

2. The method according to claim 1, wherein initiating the cleaning of the sensor comprises a user manually starting the cleaning.

3. The method according to claim 1, wherein initiating the cleaning of the sensor comprises determining that an AC signal created at the $pCO_2$ electrode is a cleaning signal.

4. The method according to claim 1, wherein the AC signals received from initiating the cleaning provide a signal function f(t).

5. The method according to claim 4, wherein the cleaning progress is determined by analysis of derivatives of the signal function f(t).

6. The method according to claim 5, wherein the analysis comprises analysis of first and/or second derivatives of the signal function f(t).

7. The method according to claim 1, wherein the dry cleaning progress is determined in cleaning intervals, each interval being generated when a predetermined criterion has been met.

8. The method according to claim 7, wherein the sensor is determined to be sufficiently cleaned when a predetermined number of intervals have been performed.

9. The method according to claim 1, wherein the information to the user is provided by a monitor connected to the sensor.

10. The method according to claim 9, wherein the monitor is kept in a cleaning mode as long as the sensor shall be cleaned.

11. A monitor for monitoring signals measured by a transcutaneous sensor comprising an electrode for measuring $pCO_2$ and an electrode for measuring pO2, both electrodes opening into a measuring surface of the sensor, the monitor being adapted to monitor a cleaning progress of said transcutaneous sensor by:
    receiving an input initiating a cleaning of the sensor,
    receiving an AC signal from the $pCO_2$ electrode in response to the receiving the input initiating the cleaning of the sensor,
    monitoring the cleaning progress by analyzing AC signals subsequently received from the $pCO_2$ electrode, and
    informing a user of a status of the cleaning progress.

12. The monitor according to claim 11, wherein the monitor is adapted for receiving input from a user and initiating the cleaning of the sensor comprises a user manually starting the cleaning by providing input to the monitor.

13. The monitor according to claim 12, herein the monitor is kept in a cleaning mode as long as the sensor is being cleaned.

14. The monitor according to claim 12, wherein the user is informed of the cleaning progress based on a number of cleaning intervals, each interval being generated when a predetermined criterion has been met.

15. The monitor according to claim 11, wherein the monitor is kept in a cleaning mode as long as the sensor is being cleaned.

16. The monitor according to claim 15, wherein the user is informed of the cleaning progress based on a number of cleaning intervals, each interval being generated when a predetermined criterion has been met.

17. The monitor according to claim 11, wherein the user is informed of the cleaning progress based on a number of cleaning intervals, each interval being generated when a predetermined criterion has been met.

* * * * *

UNITED STATES PATENT AND TRADEMARK OFFICE
CERTIFICATE OF CORRECTION

PATENT NO.         : 10,215,729 B2
APPLICATION NO.    : 15/257553
DATED              : February 26, 2019
INVENTOR(S)        : Florian Krayss et al.

It is certified that error appears in the above-identified patent and that said Letters Patent is hereby corrected as shown below:

In the Claims

Claim 1, Column 6, Line 8, "receiving an signal from the $pCO_2$ electrode" should read -- receiving an AC signal from the $pCO_2$ electrode --.

Claim 13, Column 6, Line 58, "herein the monitor" should read -- wherein the monitor --.

Signed and Sealed this
Seventh Day of May, 2019

Andrei Iancu
*Director of the United States Patent and Trademark Office*